United States Patent
Theran (10) Patent No.: US 6,244,119 B1
(45) Date of Patent: Jun. 12, 2001

(54) MULTICHANNEL PIPETTE SYSTEM AND PIPETTE TIPS THEREFOR

(75) Inventor: Michael Theran, Cheshire, CT (US)

(73) Assignee: Wallac OY, Turku (FI)

(*) Notice: Subject to any disclaimer, the term of this patent is extended or adjusted under 35 U.S.C. 154(b) by 0 days.

(21) Appl. No.: 09/365,849

(22) Filed: Aug. 3, 1999

(51) Int. Cl.[7] ............................................. B01L 3/02
(52) U.S. Cl. ............................. 73/864.17; 73/864.11; 73/863.02; 422/100
(58) Field of Search ........................ 73/863.17, 863.18, 73/863.32, 864, 864.01, 864.11, 864.16, 864.17; 422/100, 102

(56) References Cited

U.S. PATENT DOCUMENTS

| | | | |
|---|---|---|---|
| 4,734,261 | * 3/1988 | Koizumi et al. | 422/100 |
| 5,061,449 | * 10/1991 | Torti et al. | 422/100 |
| 5,915,284 | * 6/1999 | Meltzer et al. | 73/864.17 |
| 5,970,806 | * 10/1999 | Telimaa et al. | 73/864.17 |

* cited by examiner

Primary Examiner—Hezron Williams
Assistant Examiner—C D Garber
(74) Attorney, Agent, or Firm—Kubovcik & Kubovcik (57) ABSTRACT

The present invention relates generally to a multichannel pipetting system that can be used with a plurality of well plates used for medical, biological or biochemical research involving liquid materials. The system includes a multichannel pipettor and novel pipette tips having a crown that can be fitted over the opening of more than one channel. The multichannel pipettor may optionally be provided with an array of air pressure channels placed among the array of pipetting channels and enables the pipettor to aspirate and dispense a crude large volume of liquid material through the novel pipette tips of the present invention.

13 Claims, 8 Drawing Sheets

MULTICHANNEL PIPETTE SYSTEM AND PIPETTE TIPS THEREFOR

FIELD OF INVENTION

The present invention relates to a multichannel pipetting system including a multichannel pipettor and pipette tips capable of transferring small volumes of liquid samples between sample plates having different arrays of wells.

BACKGROUND OF INVENTION

Automated multichannel pipette systems used in laboratory research, especially in the biotechnology and medical fields, for simultaneously transferring a plurality of liquid samples between welled trays are known. Such systems include pipettors having a plurality of pumping devices such as syringes which comprise channels having a like number of pistons or plungers disposed therein. The pistons are connected to a moving plate to permit simultaneous movement of the pistons. A removable pipette tip is provided at the lower end of each channel.

Multichannel pipettors are commercially available that can simultaneously dispense samples or reagents into welled plates, typically 96 or 384 wells at a time from a corresponding number of channels or syringes. The welled plates have a standard size of about 3.4 inches by about 5.0 inches regardless of the number of wells and only the spacing between wells and the thickness of the walls between adjacent wells varies. For a 96 well plate, the wells are arranged in an 8×12 array with a 9 mm centerline spacing between adjacent wells. A 384 well plate has an 16×24 array of wells with a 4.5 mm centerline spacing. Well assay plates having 1,536 wells in an 32×48 array and a 2.25 mm spacing are also currently available and plates having wells spaced less than 2.25 mm apart will likely be required for future markets.

Conventional technology requires processing media to be determined and matching liquid handling equipment to be purchased. For example, if a 96 well sample plate is selected for a certain laboratory application, a 96 channel pipettor is required. On the other hand, if a 384 well sample plate is selected, a 384 channel pipettor is required. Multichannel pipettors are expensive and the requirement to specifically match a pipettor to a well plate is impractical in a constantly changing laboratory environment.

A multichannel pipettor can be used to accommodate a smaller number of test wells by mounting a fewer number of pipette tips on the pipettor. For example, a 384 channel pipettor can be used with a 96 well test plate if only one pipette tip is used for every four channels axisymmetrically. However, a standard single well of a 96 well test plate can accommodate a volume approximately four times that of a standard single well of a 384 well test plate. The dynamic volume range of each channel would require very long channels since the volume per stroke length is small due to the 4.5 mm centerline spacing requirement.

It is an object of the present invention, therefore, to provide a multichannel pipetting system and pipette tips that would allow a single multichannel pipettor to be used with different well plates without the inconveniences discussed above.

SUMMARY OF INVENTION

The present invention provides a multichannel pipetting system that can be used with different well plates. The system includes a multichannel pipettor and novel pipette tips having a crown that can be fitted over the opening of more than one channel.

In another embodiment of the invention, the multichannel pipettor is provided with an array of air pressure channels placed among the array of pipetting channels and enables the pipettor to aspirate and dispense crude large volumes of liquid material through the novel pipette tips of the present invention.

DETAILED DESCRIPTION OF THE INVENTION

The present invention is a multichannel pipette system which includes a multichannel pipettor and novel pipette tips and, optionally, an air pressure channel. The multichannel pipette system enables the use of one multichannel pipettor to accommodate all the wells of sample plates having different arrays of wells.

The multichannel pipettor of the multichannel pipette system of the present invention is not particularly limited and can include both manual and automatic pipettors although the multichannel pipette system of the invention is most useful with 384 and 96 channel pipettors.

Figures 1, 2:
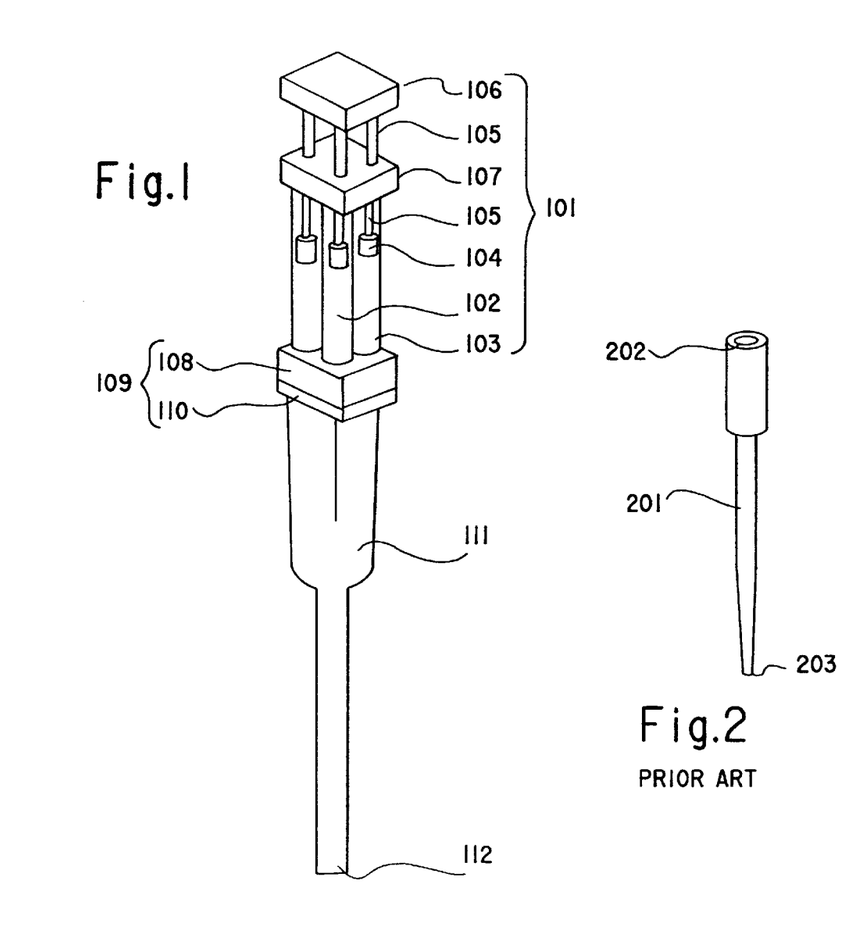
FIG. 1 is a an illustration of a portion of a multichannel pipettor and one embodiment of a pipette tip of the present invention.
FIG. 2 shows a conventional pipette tip.

FIG. 1 illustrates a portion of a multichannel pipettor of the type useful in the multichannel pipette system of the present invention in combination with an embodiment of a pipette tip of the multichannel pipette system of the present invention. The multichannel pipettor 101 includes a plurality of channels 102 having as elements thereof a tube 103, at least one plunger 104 slidably disposed inside the tube and a plunger rod 105 attached to a plunger and to a common plunger drive plate 106. The tubes are held in place by channel support plates 107 and 108 at either end of the tubes. The multichannel pipettor 101 further includes a head 109 comprising the channel support plate 108 and a means 110 for forming an air tight seal with pipette tip 111, which has a dispensing end 112. The head 109 has holes, or orifices, of generally the same diameter as the channels 102 and are aligned in the same array as the channels 102. Aspirating or dispensing is done simultaneously in each channel when the common plunger drive plate 106 pulls the plungers 104 away from the head 109 or pushes the plungers towards the head, respectively.

The tubes 103 of the multichannel pipettor 101 are typically made of glass. The plungers 104 are preferably made of an easily slidable material such as Teflon™. The channel support plates 107 and 108 are generally made of a material such as metal that is sufficiently strong to hold the channels in place and to support the pressure required to create an air tight seal between pipette tips 111 and the tip seal means 110.

The tip seal means 110 of the present invention includes any means of creating an air tight seal with a pipette tip of the present invention which, as is described below, has a crown that fits around more than one channel opening. The tip seal means 110 of the multichannel pipettor of the present invention is, preferably, a sheet of an elastomer which can be secured to the channel support plate 108. The elastomer has an appropriate flexibility and elasticity such that an air tight seal is created when a pipette tip is placed against the tip seal gasket under pressure without, at the same time, interrupting the seals formed between the tip seal means 110 and adjacent pipette tips. Preferably, the tip seal means 110 is a gasket made of a silicone sheet having a thickness of about $1/16$ to about $1/4$ inch and which compresses about $1/32$ to about $1/8$ inch when tips are pressed against the gasket.

The pipette tip 111 of the multichannel pipette system of the present invention is specially designed to enable the multichannel pipettor to be used with sample well plates having different arrays of wells. Conventional pipette tips as shown in FIG. 2 are designed to be used with only one corresponding channel of a multichannel pipettor. The conventional tip 201 has a dispensing end 203 and a crown 202 that has a circular geometry, in a plane perpendicular to an axis drawn through the center of the crown and the dispensing end, and corresponds to the opening of a single channel of a multichannel pipettor. The tip is held to the pipettor with a tapered friction fit, double O-ring arrangement, or tip seal means that both seals and holds the tip in proper orientation with a channel.

Figure 3:
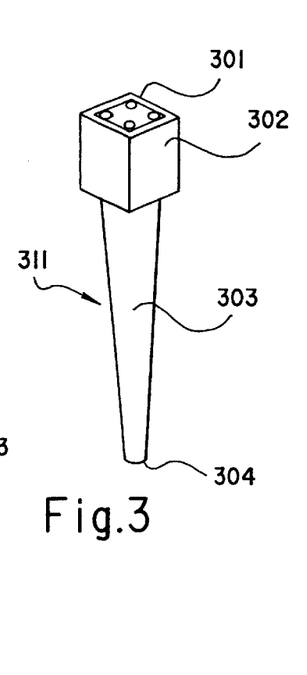
FIG. 3 is an embodiment of a pipette tip of the present invention.

The pipette tip of the present invention, on the other hand, has a crown, or reservoir end, that has a geometry that circumscribes two or more channel openings. FIG. 3 shows one embodiment of a pipette tip 311 of the present invention wherein the shape of the crown 301 of the pipette tip is such that it covers more than one channel of a multichannel pipettor. The shape of the crown 301 shown in FIG. 3 is a square although the crown can be of any convenient shape including but not limited to a rectangular or triangular shape, which circumscribes more than one channel. The crown can have rounded corners to facilitate the manufacture thereof.

As illustrated in FIG. 3, the pipette tip of the present invention has a reservoir 302 for combining the volumes of liquid aspirated and dispensed from more than one channel covered by the crown end of the tip. The dispensing tip 303 of the pipette tip is generally tapered or conical but can be cylindrical. The dispensing tip 303 has an end 304 which communicates with the reservoir and is provided with an opening 304 for a liquid sample to enter the tip when aspirating and to exit the tip when dispensing. The inside diameter of the dispensing tip 303 at the end 304 will vary depending on the size of the sample wells with which it is to be used. Such inside diameters are generally in a range of about 0.005 inches to 0.100 inches.

Figure 4:
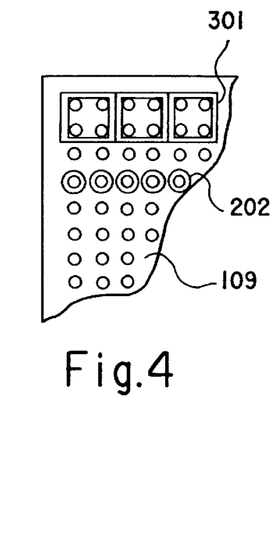
FIG. 4 compares the placement of the crown of a pipette tip of the present invention with the placement of the crown of a standard pipette tip.
Figure 5A:
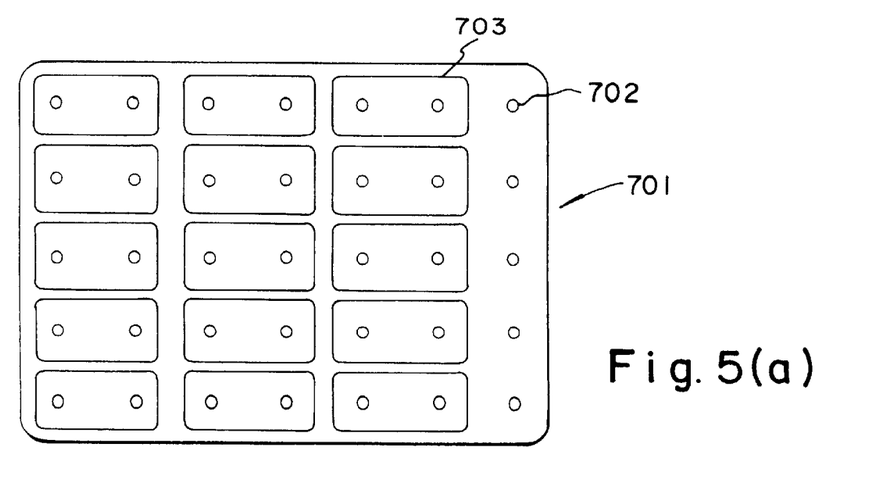
FIGS. 5(a)–5(j) illustrate embodiments of crown shapes of pipette tips and tip alignment in an arrangement of the present invention.
Figure 5B:
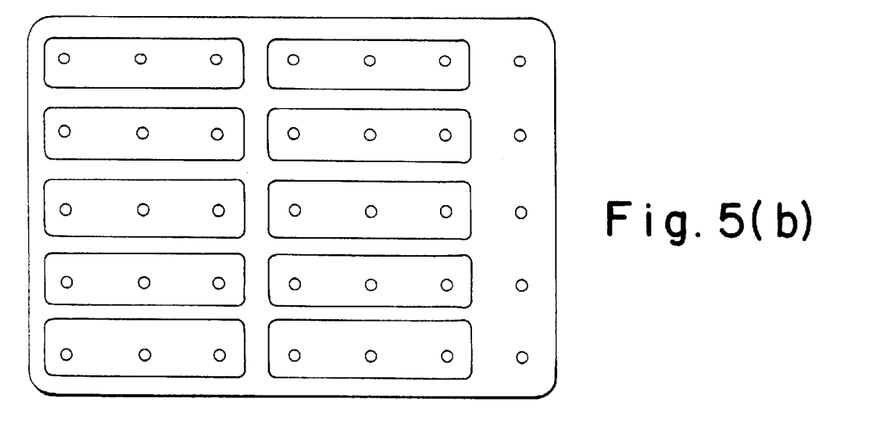
Figure 5C:
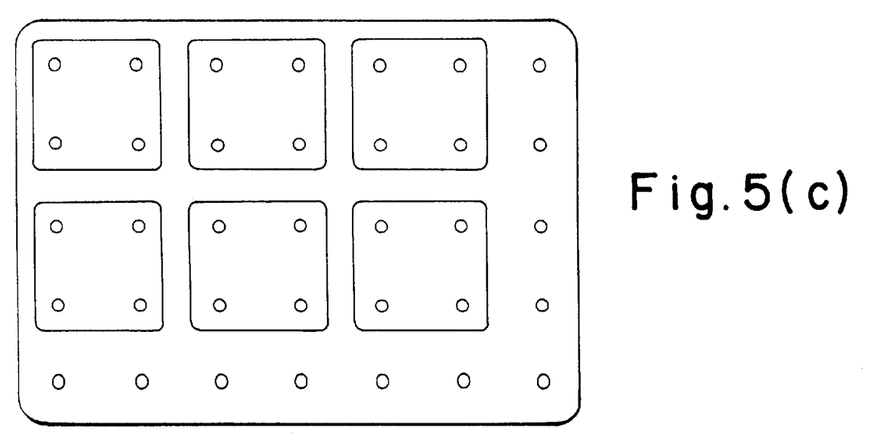
Figure 5D:
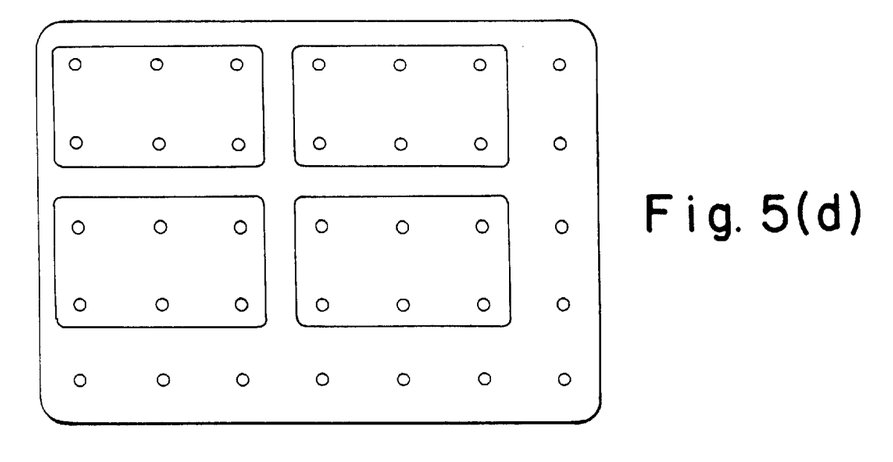
Figure 5E:
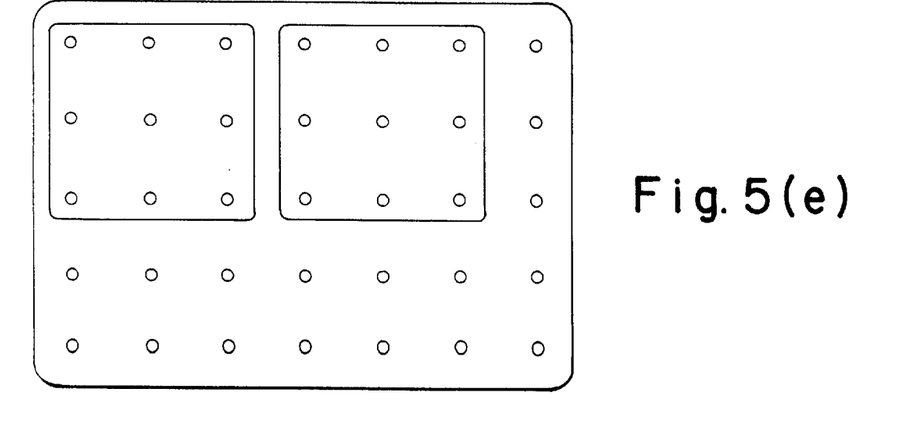
Figure 5F:
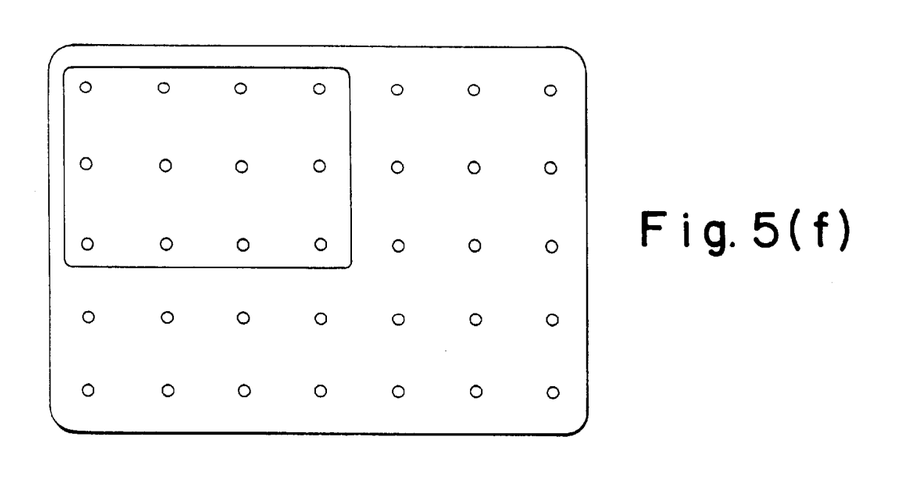
Figure 5G:
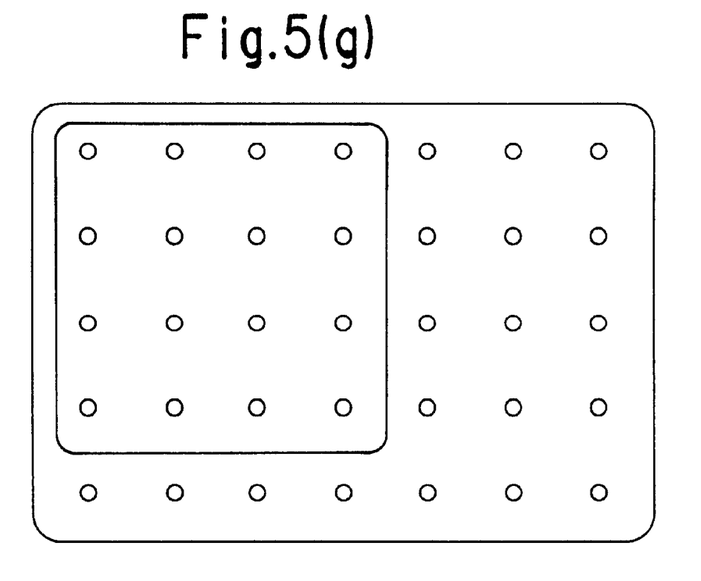
Figure 5H:
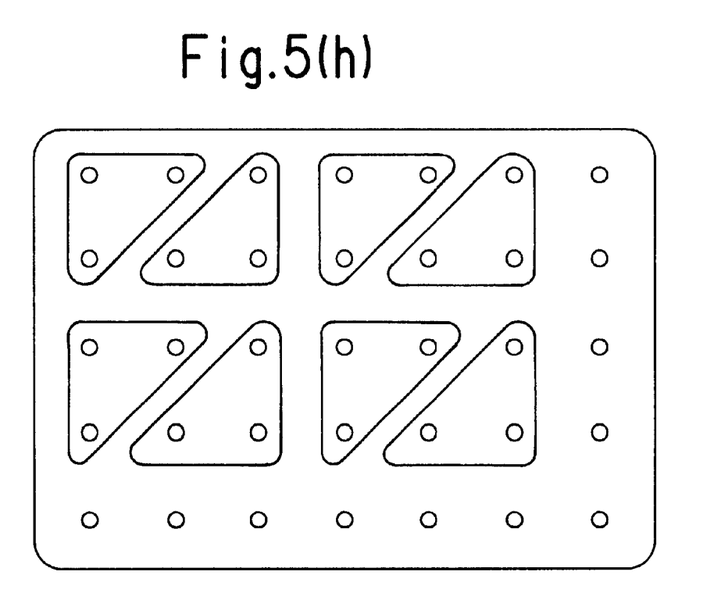
Figure 5I:
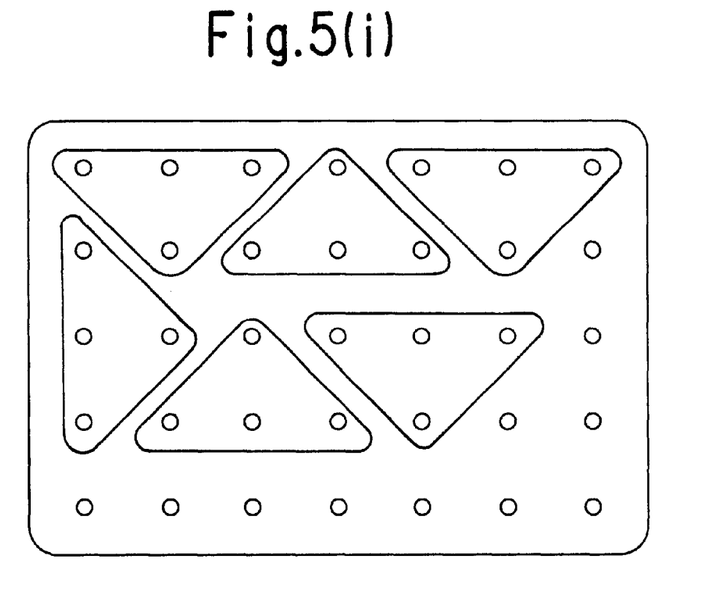
Figure 5J:
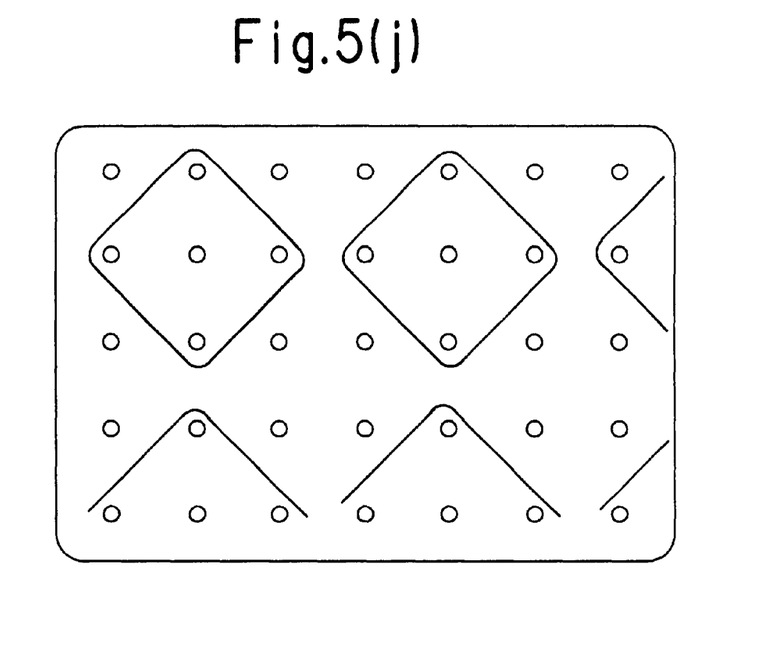

FIG. 4 compares positioning of a conventional pipette tip crown 202 as shown in FIG. 2 and a pipette tip crown 301 of the embodiment of the pipette tip of the present invention shown in FIG. 3 with respect to the openings of the channels of a multichannel pipettor. As may be seen by referring to FIG. 4, a conventional pipette tip is designed to be positioned over and seal the opening of a single channel of a multichannel pipettor. A pipette tip of the present invention, on the other hand, is designed to fit over and seal the opening of a plurality of channels of a multichannel pipettor. In the embodiment shown in FIG. 4, the pipette tip of the present invention has a square-shaped crown end 301 that fits over a 2×2 array of, i.e., four, channel openings.

FIGS. 5(a) to 5(j) illustrate other possible geometries of the crown ends of embodiments of the pipette tip of the present invention. Each of these figures shows a portion 701 of a head of a multichannel pipettor having openings 702 of the channels. Numeral 703 represents the contact area of the crown of a pipette tip with the head of the pipettor. Neither the channel openings nor the geometries of the crowns of the pipette tips is drawn to scale. The axis of the dispensing ends of the pipette tips having crown ends having the shapes shown in FIGS. 5(a)–5(j) can be chosen according to the number and orientation of wells of a well plate with which the tips are to be used. The axis can be centered in the crown as in the pipette tips shown in FIG. 3 or can be offset with respect to the center of the crown. The crown ends of the pipette tips of the present invention can be designed to enclose and seal a plurality of different channels of a multichannel pipettor depending upon the needs of a particular laboratory and the type of sample plates that are available.

The pipette tips of the present invention can be made of any material conventionally used for pipette tips of multichannel pipettors. Since many biological experiments involve material which is considered a biohazard, plastic tips are often used because they are inexpensive, easy to sterilize, and disposable. Polypropylene is a preferred material for the pipette tips of the present invention.

The pipette tips of the invention can be molded individually and held in place for mounting on a multichannel pipettor in an arrangement comprising a plastic molded sheet with holes appropriately arranged to hold the dispensing end of the appropriate shaped pipette tip. Alternatively, an arrangement of tips could be integrally molded in a single unit for easier mounting and ejecting of tips.

The pipette tips of the present invention are held in place and sealed against the head of a multichannel pipettor by an appropriate sealing means. In a presently preferred embodiment, a gasket of an elastomeric sheet, such as a silicone sheet, having holes in registration with the openings of the channels of the pipettor is secured to the bottom head of the multichannel pipettor and the crown ends of the pipette tips are pressed against the gasket by a suitable means. For example, the pipette tips can be held in a molded plastic sheet having a size corresponding substantially to the size of the bottom head of the pipettor and having holes appropriately arranged to hold the dispensing end of the appropriate shaped pipette tip. The edges of the molded plastic sheet are secured to the pipettor such that the crowns of the pipette tips are forced against the gasket with sufficient and appropriate pressure to provide an air tight seal between the tips and the gasket.

Figure 6:
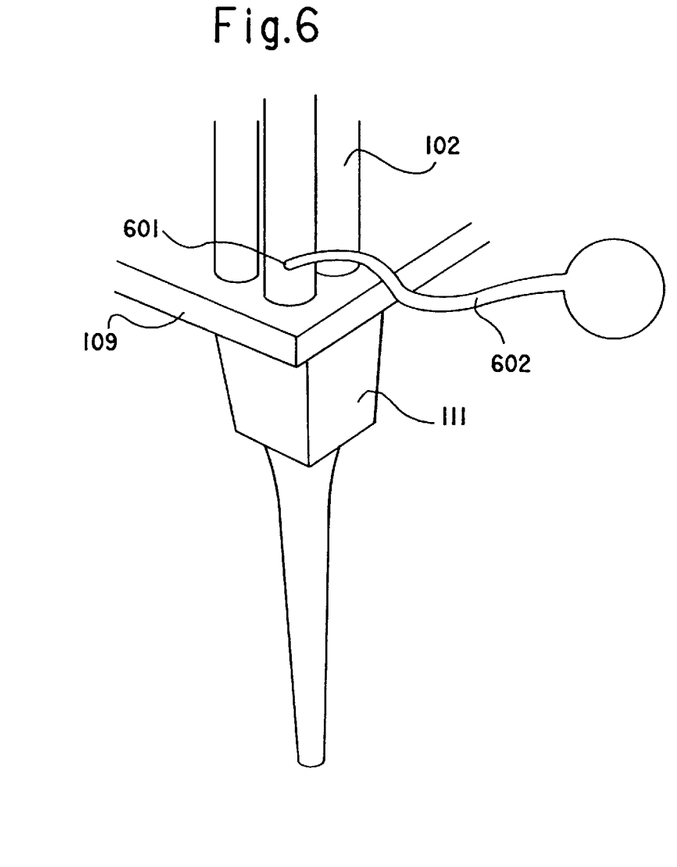
FIG. 6 is a perspective view of a portion of a multichannel pipettor showing the position of an optional air pressure channel.

FIG. 6 illustrates another embodiment of a multichannel pipette system of the present invention in which the multichannel pipettor is provided with air channels arranged in conjunction with the array of channels. The air pressure channel can be used for gross application of pressure and vacuum allowing for quick aspiration and dispensing in a timed pressure and vacuum application when precise volumes are not necessary. In a liquid dispensing mode, the air channel can be used to dispense gross reagents from a reservoir above the tips or gross aspiration to a reservoir above the tips. The use of applying air to the system can also be used in conjunction with the channels, i.e., syringes, as a non-contact dispensing pipettor. In this case, the tips are filled with the desired volume of liquid by displacing the desired volume with the syringes. Air pressure is then applied to the liquid through the air channel to quickly eject the sample.

Figure 7:
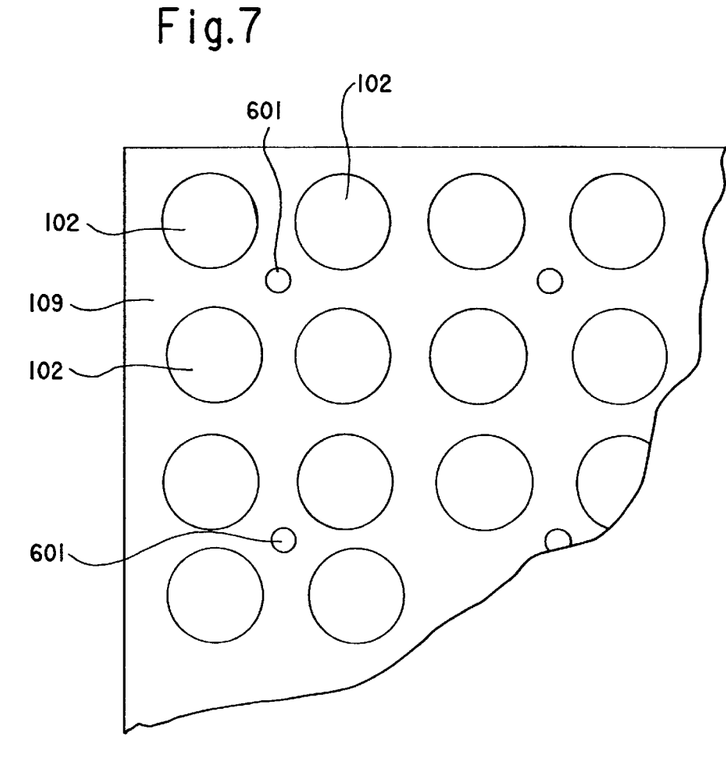
FIG. 7 is the bottom view of a head of a multichannel pipettor showing the position of an orifice of an optional air pressure channel.

As shown in FIG. 6, the air pressure channel 601 includes tubing 602 positioned between four channels 102 of the multichannel pipettor. The air pressure channels 601 form another array of holes in the multichannel pipettor head 109. Such an array is partially illustrated in FIG. 7. FIG. 7 shows the positioning of the air pressure channels 601 in the centers of arrays of four channels 102 of a multichannel pipettor head 109.

Figure 8A:
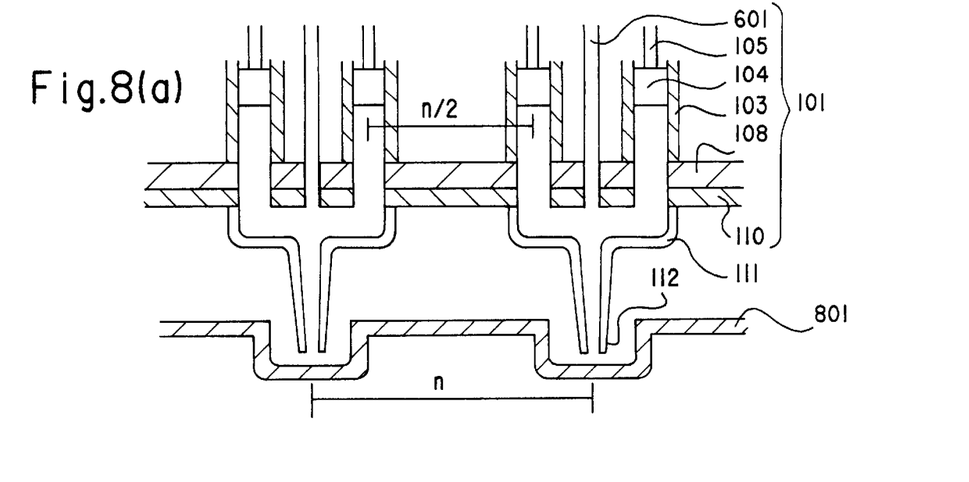
FIGS. 8(a)–8(c) show a multichannel pipetting system using the same multichannel pipettor for aspirating and dispensing into three different sample plates.
Figure 8B:
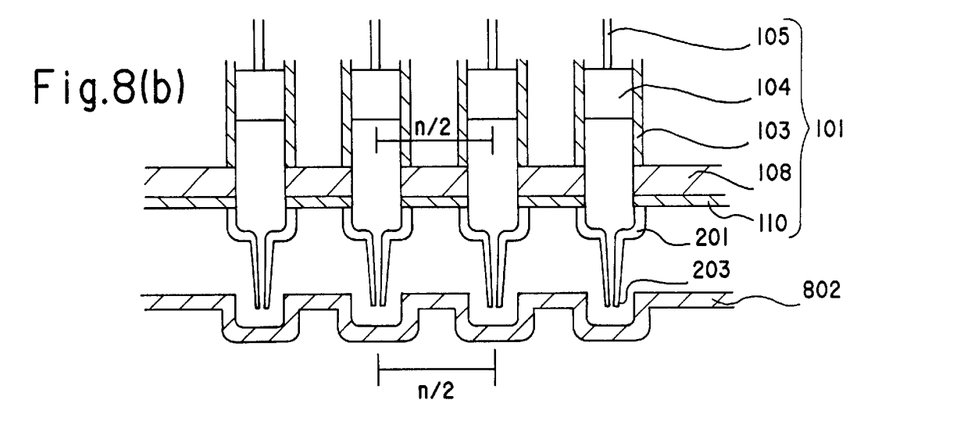
Figure 8C:
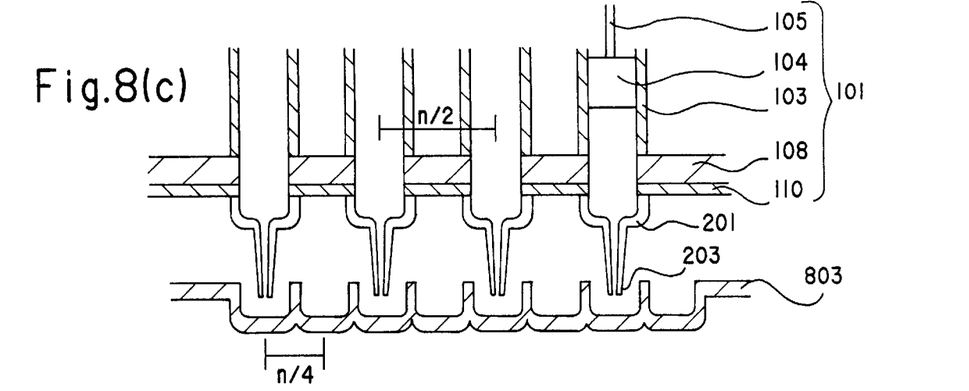

FIG. 8 illustrates how the multichannel pipette system of the present invention allows a single multichannel pipettor to be used to aspirate and dispense liquid samples among different 3.4 inch by 5.0 inch sample plates. FIG. 8 shows the tube 103, plunger 104, rod 105, channel support plate 108, and the tip seal gasket 110 of a multichannel pipettor 101 of the multichannel pipetting system of the present invention. In each of FIGS. 8(a) to 8(c), the distance between the center of the channels is n/2 mm, where n could be, for example, between 1 and 10 mm.

FIG. 8(a), shows a pipette tip of the present invention 111 used for a sample plate 801 where the distance between the centers of adjacent wells is n mm. Each of the pipette tips in FIG. 8(a) covers four channels of the multichannel pipettor. The distance between dispensing ends 112 of adjacent pipette tips is n mm. The tips 111 are directly over the center of the wells of sample plate 801, which wells are also n mm apart. FIG. 8(b) illustrates the same multichannel pipettor 101 used for a sample plate 802 where the distance between the centers of the adjacent wells is n/2 mm. The pipette tips in FIG. 8(b) are conventional pipette tips 201 covering only one channel of the multichannel pipettor 101 where the dispensing ends 203 of the adjacent pipette tips are n/2 mm apart from each other and directly over the wells of the sample plate 802.

In FIG. 8(c), if the ends of the conventional pipette tip 201 are small enough, the same multichannel pipettor 101 can also be used to accommodate every other well of a sample plate 803 where the distance between the centers of the adjacent wells is n/4. Therefore, the multichannel pipetting system of the present invention accommodates at least two sizes of sample plates directly and with proper indexing of the pipettor, or the sample plate, can be used with a third size of sample plate.

A preferred embodiment of the multichannel pipette system of the present invention includes a 384 multichannel pipettor with channels arranged in a 16×24 array. Each channel has an inside diameter of from about 1–3 mm with the center of each channel 4.5 mm apart. Using conventional pipette tips, the 384 multichannel pipettor can be used to accommodate a 384 well plate with wells 4.5 mm apart in a 16×24 array and with an appropriate plate positioning stage can also accommodate a 1,536 well plate with wells 2.25 mm apart in an 32×48 array. If the 384 multichannel pipettor is fitted with a pipette tip of the present invention having a crown that covers a 2×2 array of channels, the dispensing ends of the pipette tips will be spaced 9 mm apart and the multichannel pipette system can aspirate and dispense from either a 96 well plate, from ¼ of the wells of a 384 well plate, or from 1/16 of the wells of a 1,536 well plate.

The pipette tip of the present invention which encompasses four channels in a 2×2 array such that the spacing between the dispensing ends of the tips is 9 mm combines the volume that can be aspirated from four of the channels of a 384 well plate and provides the correct number and spacing of tips to accommodate a standard 96 well plate.

Using FIG. 8 to illustrate the preferred embodiment, if sample plate 802 is a standard 384 well sample plate and pipette tip 201 is a conventional pipette tip, it can be seen that the same multichannel pipettor 101 can be used to aspirate and dispense liquid material into either a 384 well sample plate or a 1,536 well sample plate 803 or, with the use of the pipette tip of the present invention 111, into a 96 well sample plate 801.

FIG. 8(a) also illustrates the use of an air pressure channel 601 with the pipette tips of the present invention 111 to provide for the optional quick gross aspirating of dispensing of large volumes of material. The diameter of the air pressure channel is, for example, about 1 mm.

Although the present invention has been described in conjunction with certain preferred embodiments, the present invention is not intended to be limited to these embodiments. Instead the present invention includes all those embodiments within the scope and spirit of the appended claims.

What is claimed is:

1. A multichannel pipetting system comprising:

a multichannel pipettor comprising a plurality of channels arranged in a two dimensional array, each channel having an aspirating and dispensing end, and means for simultaneous aspirating and dispensing in all channels;

a head comprising a channel support plate placed at said aspirating and dispensing end of the channels, said channel support plate having a plurality of holes corresponding to said plurality of channels and arranged in the same array as said plurality of channels such that the end of each channel is flush with the channel support plate and aligned with a hole of said channel support plate;

a plurality of pipette tips, each tip having a crown and a dispensing tip at opposite ends, said crown having a shape sufficient to be sealed over more than one hole of said channel plate, and a means for creating an air tight seal between said pipette tips and said channel support plate.

2. The multichannel pipetting system as defined in claim 1, wherein the means for creating an air tight seal is a tip seal gasket consisting of an elastomer sheet with a plurality of holes in an array corresponding to the array of holes of said channel support plate and having sufficient resilience such that an airtight seal is created when a pipette tip covering one or more of the channels is pressed against the tip seal gasket.

3. The multichannel pipetting system as defined in claim 1, wherein the array of channels is a 16 by 24 array wherein a distance between the center of the channels is about 4.5 mm and an inner diameter of each channel is in a range of about 1–3 mm.

4. The multichannel pipettor as defined in claim 3, wherein the crown of each pipette tip completely covers four channels in a 2 by 2 array and the dispensing tips of adjacent pipette tips are spaced apart about 9 mm.

5. A pipette tip for use with a multichannel pipettor comprising:

a proximal crown end to be sealed against said multichannel pipettor; a distal dispensing tip end through which liquid material is to be aspirated and dispensed;

wherein said proximal crown end has a geometry such that the pipette tip can be fitted over more than one channel of said multichannel pipettor.

6. The pipette tip of claim 5, wherein the geometry of the crown end is rectangular or triangular.

7. The pipette tip of claim 6, wherein the geometry of the crown end is square.

8. An arrangement of pipette tips for use with a multichannel pipettor and comprising a support plate and, supported therein, an array of a plurality of pipette tips, wherein each pipette tip comprises a proximal crown end to be sealed against said multichannel pipettor and a distal dispensing tip end through which liquid material is to be aspirated and dispensed;

wherein said proximal crown end has a geometry such that the pipette tip can be fitted over more than one channel of said multichannel pipettor.

9. The arrangement of pipette tips defined in claim 8, wherein said array of tips is an 8×12 array.

10. The arrangement of pipette tips defined in claim 9, wherein the dispensing tip ends of adjacent pipette tips are spaced 9 mm apart along each dimension of said array.

11. The multichannel pipetting system of claim 1, further comprising an air pressure channel provided in the center of each 2 by 2 array of channels.

12. The multichannel pipetting system of claim 11 wherein each air pressure channel is connected to an air pumping mechanism.

13. The multichannel pipetting system of claim 10 wherein each air pressure channel is attached to a liquid pumping mechanism.

* * * * *